United States Patent
Lazarev et al.

(10) Patent No.: US 12,094,609 B2
(45) Date of Patent: Sep. 17, 2024

(54) DIFFRACTOMETER-BASED GLOBAL IN SITU DIAGNOSTIC SYSTEM FOR ANIMALS

(71) Applicant: Arion Diagnostics, Inc., Petaluma, CA (US)

(72) Inventors: Alexander Lazarev, Lake Forest, CA (US); Pavel Lazarev, Menlo Park, CA (US); Delvin Tai Wai Yuk, Atherton, CA (US)

(73) Assignee: Arion Diagnostics, Inc., Petaluma, CA (US)

(\*) Notice: Subject to any disclaimer, the term of this patent is extended or adjusted under 35 U.S.C. 154(b) by 439 days.

(21) Appl. No.: 17/448,886

(22) Filed: Sep. 26, 2021

(65) Prior Publication Data
US 2022/0013227 A1 Jan. 13, 2022

Related U.S. Application Data

(63) Continuation of application No. 17/593,845, filed as application No. PCT/US2021/037238 on Jun. 14, 2021.
(Continued)

(51) Int. Cl.
*G16H 50/20* (2018.01)
*A61B 5/00* (2006.01)
(Continued)

(52) U.S. Cl.
CPC ............. *G16H 50/20* (2018.01); *A61B 5/00* (2013.01); *A61B 5/4312* (2013.01); *G01N 23/20* (2013.01);
(Continued)

(58) Field of Classification Search
CPC ........ G16H 50/20; G16H 10/40; G16H 10/60; G16H 30/20; G16H 40/63; G16H 40/67;
(Continued)

(56) References Cited

U.S. PATENT DOCUMENTS

| 5,717,733 A | 2/1998 | Kurbatov et al. |
| 6,175,117 B1 | 1/2001 | Komardin et al. |
| (Continued) | | |

FOREIGN PATENT DOCUMENTS

| KR | 20180076702 A | 7/2018 |
| WO | 2021257451 A1 | 12/2021 |
| WO | 2021257457 A1 | 12/2021 |

OTHER PUBLICATIONS

Ghammraoui et al., "Maximum-likelihood estimation of scatter components algorithm for x-ray coherent scatter computed tomography of the breast", Physics in Medicine & Biology, vol. 61, pp. 3164-3179. (Year: 2016).*

(Continued)

*Primary Examiner* — Kiho Kim
(74) *Attorney, Agent, or Firm* — MLO, a professional corp.

(57) ABSTRACT

An animal-tissue analysis and communication system produces a quantitative-diagnostic indicator for animal-tissue analyzed by the system. The system includes an animal-tissue-analyzer subsystem with at least one animal-tissue analyzer constructed to analyze animal tissue and to produce an quantitative-diagnostic indicator. The system also includes a two-way communication subsystem constructed to allow the animal-tissue-analyzer subsystem to send and receive information relevant to the quantitative-diagnostic indicator. The animal-tissue-analyzer subsystem includes at least one tissue diffractometer operatively coupled to a computer database over a network, and is configured for acquisition and transfer of animal-tissue data, and transfer to the computer database over the network. A computer processor is operatively coupled to the tissue diffractometer, and configured to receive, transmit and process the animal-tissue data from the diffractometer to the computer database, (Continued)

using a data analytics algorithm that provides a computer-aided quantitative-diagnostic indicator for a given animal-tissue sample.

26 Claims, 11 Drawing Sheets

Related U.S. Application Data

(60) Provisional application No. 63/039,340, filed on Jun. 15, 2020.

(51) Int. Cl.

| | |
|---|---|
| *G01N 23/20* | (2018.01) |
| *G01N 23/201* | (2018.01) |
| *G01N 33/483* | (2006.01) |
| *G06F 21/60* | (2013.01) |
| *G06N 3/08* | (2023.01) |
| *G06Q 20/08* | (2012.01) |
| *G06Q 20/32* | (2012.01) |
| *G16H 10/40* | (2018.01) |
| *G16H 10/60* | (2018.01) |
| *G16H 30/20* | (2018.01) |
| *G16H 40/63* | (2018.01) |
| *G16H 40/67* | (2018.01) |

(52) U.S. Cl.
CPC ....... *G01N 23/201* (2013.01); *G01N 33/4833* (2013.01); *G06F 21/602* (2013.01); *G06N 3/08* (2013.01); *G06Q 20/085* (2013.01); *G06Q 20/325* (2013.01); *G16H 10/40* (2018.01); *G16H 10/60* (2018.01); *G16H 30/20* (2018.01); *G16H 40/63* (2018.01); *G16H 40/67* (2018.01); *G01N 2223/0566* (2013.01); *G01N 2223/6126* (2013.01)

(58) Field of Classification Search
CPC ........ G16H 50/30; A61B 5/00; A61B 5/4312; G01N 23/20; G01N 23/201; G01N 33/4833; G01N 2223/0566; G01N 2223/6126; G06F 21/602; G06F 21/6245; G06N 3/08; G06N 3/04; G06N 20/00; G06Q 20/085; G06Q 20/325
See application file for complete search history.

(56) References Cited

U.S. PATENT DOCUMENTS

| | | | |
|---|---|---|---|
| 6,483,891 B1 | 11/2002 | Lazarev et al. | |
| 2003/0014418 A1* | 1/2003 | Adler | G06F 21/6245 |
| 2006/0015265 A1* | 1/2006 | Raich | G01N 23/20 |
| | | | 702/22 |
| 2007/0032832 A1* | 2/2007 | Feher | H04L 5/1453 |
| | | | 607/32 |
| 2015/0269323 A1 | 9/2015 | Ginsburg | |
| 2016/0235372 A1* | 8/2016 | Schneider | G16Z 99/00 |
| 2017/0362585 A1* | 12/2017 | Wang | G06T 11/006 |
| 2018/0038845 A1 | 2/2018 | Zimmermann et al. | |
| 2018/0122499 A1 | 5/2018 | Austin et al. | |
| 2019/0113451 A1 | 4/2019 | Weissleder et al. | |
| 2020/0098476 A1 | 3/2020 | Loscutoff et al. | |
| 2022/0008027 A1 | 1/2022 | Lazarev et al. | |
| 2022/0013227 A1 | 1/2022 | Lazarev et al. | |
| 2022/0013233 A1 | 1/2022 | Lazarev et al. | |
| 2022/0415505 A1 | 12/2022 | Lazarev et al. | |

OTHER PUBLICATIONS

Graewet et al., "Impact and progress in small and wide angle X-ray scattering (SAXS and WAXS)", Current Opinion in Structural Biology, vol. 23, pp. 748-754. (Year: 2013).*

Fagundes et al., "Structural characterization of canine mammary tissue by x-ray diffraction", Radiation Physics and Chemistry, vol. 155, pp. 22-25. (Year: 2019).*

Park, Hye Lyun, Authorized Officer, Korean Intellectual Property Office, "International Search Report" in connection with related International Application No. PCT/US2021/037238, dated Oct. 5, 2021, 5 pgs.

Park, Hye Lyun, Authorized Officer, Korean Intellectual Property Office, "Written Opinion of the International Searching Authority" in connection with related International Application No. PCT/US2021/037238, dated Oct. 5, 2021, 5 pgs.

Rodriguez, Kari, Authorized Officer, Commissioner for Patents, U.S. Patent and Trademark Office, "International Search Report" in connection with related International Application No. PCT/US2021/037224, dated Sep. 29, 2021, 3 pgs.

Rodriguez, Kari, Authorized Officer, Commissioner for Patents, U.S. Patent and Trademark Office, "Written Opinion of the International Searching Authority" in connection with related International Application No. PCT/US2021/037224, dated Sep. 29, 2021, 6 pgs.

Notice of Allowance and Fees dated Feb. 6, 2023 for U.S. Appl. No. 17/593,846.

Office Action dated Mar. 22, 2023 for U.S. Appl. No. 17/448,888.

James, "A Review of Low Angle Fibre Diffraction in the Diagnosis of Disease", British Journal of Medicine & Medical Research, 3(2): 383-397, Feb. 19, 2013.

James, "Fiber diffraction of skin and nails provides an accurate diagnosis of malignancies", Int. J. Cancer: 125, 133-138, 13 pages, Jul. 2009.

Ortiz et al., "Biomarkers of disease in human nails: a comprehensive review", Critical Reviews in Clinical Laboratory Sciences, Oct. 7, 2021, 18 pgs, Taylor & Francis Group.

European Search Report dated May 24, 2024 for European Patent Office Patent Application No. 21826535.3.

* cited by examiner

DIFFRACTOMETER-BASED GLOBAL IN SITU DIAGNOSTIC SYSTEM FOR ANIMALS

CROSS-REFERENCE TO RELATED APPLICATIONS

This application is a continuation of U.S. patent application Ser. No. 17/593,845, filed Sep. 26, 2021 and entitled "Diffraction-Based Global In Vitro Diagnostic System", which application is a U.S. national phase application of International Application No. PCT/US2021/037238, filed Jun. 14, 2021, which in turn claims priority to U.S. Provisional Patent Application Ser. No. 63/039,340, filed Jun. 15, 2020, the disclosures which are incorporated herein by reference.

FIELD OF THE DISCLOSURE

The proposed invention relates to a global diagnostic data system for providing structural analysis of animal tissue, such as tissue from an animal's internal organs. The invention can be suitably used in veterinary medical applications.

BACKGROUND

The uniqueness of the x-ray method is its accessibility, absolute painlessness and the ability to get a detailed picture of the state of bone structures and some internal organs. Due to these features, x-ray examination is widely used in veterinary medicine. The scope of radiography is extensive. It is the most informative method of research and is used in the diagnosis of the musculoskeletal system; internal organs of the abdominal cavity; neurology; ENT; oral cavity and other diseases. It is also important to study the internal organs for the presence of foreign bodies and neoplasms, including malignant ones.

The authors consider the possibility of using small-angle x-ray spectroscopy to study the structure of potential cancer sites (see, P. Lazarev et al., "Human Tissue X-ray Diffraction: Breast, Brain, and Prostate", Proceedings of the 22nd Annual International Conference of the IEEE Engineering in Medicine and Biology Society (Cat. No. 00CH37143) (Vol. 4, pp. 3230-3233). (2000, July). Authors of this article report that upon the incidence of x-ray radiation onto a sample, part of the radiation goes through the object unaffected, part is absorbed and the rest is scattered. Absorption and incoherent scattering are related to the atomic composition and density of the sample; coherent scattering is related to the molecular structure of the sample. The intensity of coherently scattered radiation, as a function of angle, is a function of the molecular structure of the object being irradiated. Every molecular structure has its own "signature" scattering pattern. Therefore, by studying scattering patterns of various materials, we can characterize them and recognize them when encountered again. The authors of the article described this technique in relation to the tissues of the human body, but it is obvious that this technique is applicable to animal tissues. Biological tissues are also periodic, though the period (size of a unit) may be much greater than that of a crystal. The bigger the unit, the smaller the angle at which it will produce the first and other peaks in its scattering pattern. In studying biological tissues, we are dealing with units of large sizes, which dictates the need for small-angle x-ray scattering.

Early detection of cancer may be correlated with increased survival rates. x-ray techniques are widely used as diagnostic tools for detecting the presence of cancer internal organs of animals but can suffer from poor contrast and other factors that can increase the difficulty of diagnosis based on these methods.

SUMMARY OF INVENTION

In one aspect, disclosed herein are an animal-tissue analysis and communication system that produces a quantitative-diagnostic indicator for animal-tissue analyzed by the system, and includes: (i) an animal-tissue-analyzer subsystem that includes at least one animal-tissue analyzer constructed to analyze animal tissue and to produce an quantitative-diagnostic indicator; and (ii) a two-way communication subsystem constructed to allow the animal-tissue-analyzer subsystem to send and receive information relevant to the quantitative-diagnostic indicator.

The system is constructed to analyze and communicate a quantitative indicator of either live or dead animal tissue. In other words, the system is usable for in vivo and in vitro applications.

The animal-tissue-analyzer subsystem includes at least one tissue diffractometer operatively coupled to a computer database over a network, and is configured for acquisition of animal-tissue data chosen from the group consisting of in situ image data, in situ diffraction pattern data, and subject data, and transfer of the animal-tissue data to the computer database over the network. Preferably, at least one computer processor is operatively coupled to the at least one tissue diffractometer, and wherein the at least one computer processor is configured to receive the animal-tissue data from the at least one diffractometer, transmit the animal-tissue data to the computer database; and process the animal-tissue data using a data analytics algorithm that provides a quantitative-diagnostic indicator for a given animal-tissue sample.

The animal-tissue analyzer subsystem may include: (a) one or more tissue diffractometers intended for structural analysis of a tissue of animal's internal organs operatively coupled to a computer database over a network, wherein a tissue diffractometers of the one or more tissue diffractometers is configured for acquisition and transfer of in situ image data, in situ diffraction pattern data, subject data, or any combination thereof to the computer database over the network; and (b) one or more computer processors operatively coupled to the one or more tissue diffractometers, wherein the one or more computer processors are individually or collectively configured to: (i) receive the in situ image data, in situ diffraction pattern data, subject data, or any combination thereof from the one or more tissue diffractometers; (ii) transmit the in situ image data, in situ diffraction pattern data, subject data, or any combination thereof to the computer database; and (iii) process the in situ image data, in situ diffraction pattern data, subject data, or any combination thereof for an individual animal using a data analytics algorithm that provides a quantitative-diagnostic indicator for the individual animal.

In one embodiment of the disclosed invention, the system further comprises a user interface that allows an individual animal owner, their agent, such as an animal trainer, or their veterinary services provider, to upload the individual animal's in situ image data, in situ diffraction pattern data, animal data, or any combination thereof to the computer database in exchange for processing of the individual animal's in situ image data, in situ diffraction pattern data, animal data, or any combination thereof to receive the quantitative-diagnostic indicator for the individual animal. In another embodiment of the disclosed system the user interface is further configured to allow an individual animal owner or their veterinary services provider to make payments or upload a consent form signed by individual animal owner. In yet another embodiment of the present disclosure the system comprises one or more tissue diffractometers located in one or more different geographic locations.

In still another embodiment of the disclosed system, the one or more tissue diffractometers comprise a data encryption device that includes a global positioning system (GPS) positioning sensor and generates encrypted in situ image data, in situ diffraction pattern data, animal data, or any combination thereof, which encrypted in situ image data, in situ diffraction pattern data, animal data, or any combination thereof that is transferred to the computer database tracks changes in location of the one or more tissue diffractometers. In one embodiment of the disclosed system, the one or more tissue diffractometers are configured to perform small angle x-ray scattering (SAXS) measurements. In another embodiment of the disclosed system the one or more tissue diffractometers are configured to perform wide angle x-ray scattering (WAXS) measurements. In yet another embodiment of the disclosed system the computer database resides on a central server. In still another embodiment of the disclosed system the computer database resides in the cloud. In one embodiment of the disclosed system the in situ image data, in situ diffraction pattern data, animal data, or any combination thereof transferred to the computer database is depersonalized prior to transfer.

In another embodiment of the disclosed system, a key for mapping depersonalized in situ image data, in situ diffraction pattern data, animal data, or any combination thereof stored in the computer database is stored in a local institutional database or in the individual personal files of the animal owner. In yet another embodiment of the disclosed system, the data analytics algorithm comprises a statistical analysis of diffraction pattern data or a function thereof. In still another embodiment of the disclosed system, the statistical analysis comprises determination of a pairwise distance distribution function, determination of a Patterson function, a calculation of a Porod invariant, a cluster analysis, a dispersion analysis, determination of one or more molecular structural periodicities, or any combination thereof. In one embodiment of the disclosed system, the statistical analysis comprises a determination of a structural periodicity of collagen, one or more lipids, and a tissue. In another embodiment of the disclosed system, the data analytics algorithm comprises a machine learning algorithm.

In yet another embodiment of the disclosed system, the machine learning algorithm comprises a supervised learning algorithm, an unsupervised learning algorithm, a semi-supervised learning algorithm, a reinforcement learning algorithm, a deep learning algorithm, or any combination thereof. In still another embodiment of the disclosed system the machine learning algorithm is a deep learning algorithm. In one embodiment of the disclosed system, the deep learning algorithm is a convolutional neural network, a recurrent neural network, or a recurrent convolutional neural network. In another embodiment of the disclosed system, the machine learning algorithm is trained using a training dataset comprising image data, diffraction pattern data, subject data, or any combination thereof stored in the computer database for a specific pathology or physiological norm group. In yet another embodiment of the disclosed system, the training dataset is updated as new in situ image data, in situ diffraction pattern data, animal data, or any combination thereof is uploaded to the computer database. In still another embodiment of the disclosed system, the animal data comprises an individual animal's age, sex, weight, body condition score (BCS), ancestry data, genetic data, behavioral data, or any combination thereof. In one embodiment of the disclosed system, the quantitative-diagnostic indicator for the individual animal comprises an indicator of a likelihood that the individual animal has cancer. In another embodiment of the disclosed system, the indicator of the likelihood that the individual animal has cancer is an indicator of the likelihood that the individual animal has breast cancer. In yet another embodiment of the disclosed system, the quantitative-diagnostic indicator for the individual animal comprises a diagnosis that the individual animal has a cancer. In still another embodiment of the disclosed system, the diagnosis that the individual animal has cancer is a diagnosis that the individual animal has breast cancer.

In another aspect, disclosed herein are methods comprising: acquiring data comprising in situ image data, in situ diffraction pattern data, animal data, or any combination thereof for an individual animal using one of a plurality of tissue diffractometers operatively coupled to a computer database over a network, wherein the plurality of tissue diffractometers is configured for acquisition and transfer of the data to the computer database over the network; using one or more computer processors operatively coupled to the plurality of tissue diffractometers to: receive the data comprising in situ image data, in situ diffraction pattern data, animal data, or any combination thereof from the plurality of tissue diffractometers that are operatively coupled to the computer database over the network and are configured for transfer of the data comprising in situ image data, in situ diffraction pattern data, animal data, or any combination thereof to the computer database over the network; transmit the data comprising the in situ image data, in situ diffraction pattern data, animal data, or any combination thereof to the computer database; and process the data comprising the in situ image data, in situ diffraction pattern data, animal data, or any combination thereof for the individual animal using a data analytics algorithm that provides a quantitative-diagnostic indicator for the individual animal.

In some embodiments, the method may further comprise providing a user interface that allows the individual animal owner or their veterinary services provider to upload the individual animal's data comprising in situ image data, in situ diffraction pattern data, animal data, or any combination thereof to the computer database in exchange for processing of the individual animal's data to receive the quantitative-diagnostic indicator for the individual animal. In some embodiments, the user interface is further configured to allow the individual animal owner or their veterinary services provider to make payments or upload an individual consent form signed by animal owner. In some embodiments, the plurality of tissue diffractometers comprises two or more tissue diffractometers located in two or more different geographic locations. In some embodiments, the plurality of tissue diffractometers comprises a data encryption device that includes a global positioning system (GPS) positioning sensor and generates encrypted data, and the encrypted data transferred to the computer database track changes in locations of the plurality of tissue diffractometers. In some embodiments, the plurality of tissue diffractometers, are configured to perform small angle x-ray scattering (SAXS) measurements. In some embodiments, the plurality of tissue diffractometers, are configured to perform wide angle x-ray scattering (WAXS) measurements.

In some embodiments, the plurality of tissue diffractometers, are further configured to perform animal breast studies. In some embodiments, a set of target coordinates for directing an x-ray beam are determined from animal breast research data. In some embodiments, the computer database resides on a central server. In some embodiments, the computer database resides in the cloud. In some embodiments, the data comprising in situ image data, in situ diffraction pattern data, animal data, or any combination thereof transferred to the computer database are depersonalized prior to transfer. In some embodiments, a key for mapping the depersonalized data stored in the computer database to the individual animal is stored in a local institutional database or in the personal files of animal owner.

In some embodiments, the data analytics algorithm comprises a statistical analysis of diffraction pattern data or a function thereof. In some embodiments, the statistical analysis comprises determination of a pair-wise distance distribution function, determination of a Patterson function, a calculation of a Porod invariant, a cluster analysis, a dispersion analysis, determination of one or more molecular structural periodicities, or any combination thereof.

In some embodiments, the statistical analysis comprises a determination of a structural periodicity of collagen. In some embodiments, the statistical analysis comprises a determination of a structural periodicity of a lipid. In some embodiments, the statistical analysis comprises a determination of a structural periodicity of a tissue. In some embodiments, the data analytics algorithm comprises a machine learning algorithm.

In some embodiments, the machine learning algorithm comprises a supervised learning algorithm, an unsupervised learning algorithm, a semi-supervised learning algorithm, a reinforcement learning algorithm, a deep learning algorithm, or any combination thereof. In some embodiments, the machine learning algorithm is a deep learning algorithm. In some embodiments, the deep learning algorithm is a convolutional neural network, a recurrent neural network, or a recurrent convolutional neural network. In some embodiments, the machine learning algorithm is trained using a training dataset comprising in situ image data, in situ diffraction pattern data, animal data, or any combination thereof stored in the computer database for a specific pathology or physiological norm group. In some embodiments, the training dataset is updated as new data comprising new in situ image data, in situ diffraction pattern data, animal data, or any combination thereof are uploaded to the computer database.

In some embodiments, the animal data comprises an individual animal's age, sex, weight, body condition score (BCS), ancestry data, genetic data, behavioral data, or any combination thereof. In some embodiments, the quantitative-diagnostic indicator for the individual animal comprises an indicator of the likelihood that the individual animal has cancer. In some embodiments, the indicator of the likelihood that the individual animal has cancer is an indicator of the likelihood that the individual animal has breast cancer. In some embodiments, the quantitative-diagnostic indicator for the individual animal comprises a diagnosis that the individual animal has cancer. In some embodiments, the diagnosis that the individual animal has cancer is a diagnosis that the individual animal has breast cancer. In some embodiments, the method further comprises repeating a)-b) at one or more subsequent time points to monitor a disease state of the individual animal as the individual animal undergoes a therapeutic treatment. In some embodiments, a rate of change of the disease state of the individual animal as indicated by the quantitative-diagnostic indicator provides a measure of the efficacy of the therapeutic treatment.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying Figures where:

DETAILED DESCRIPTION

Figure 1:
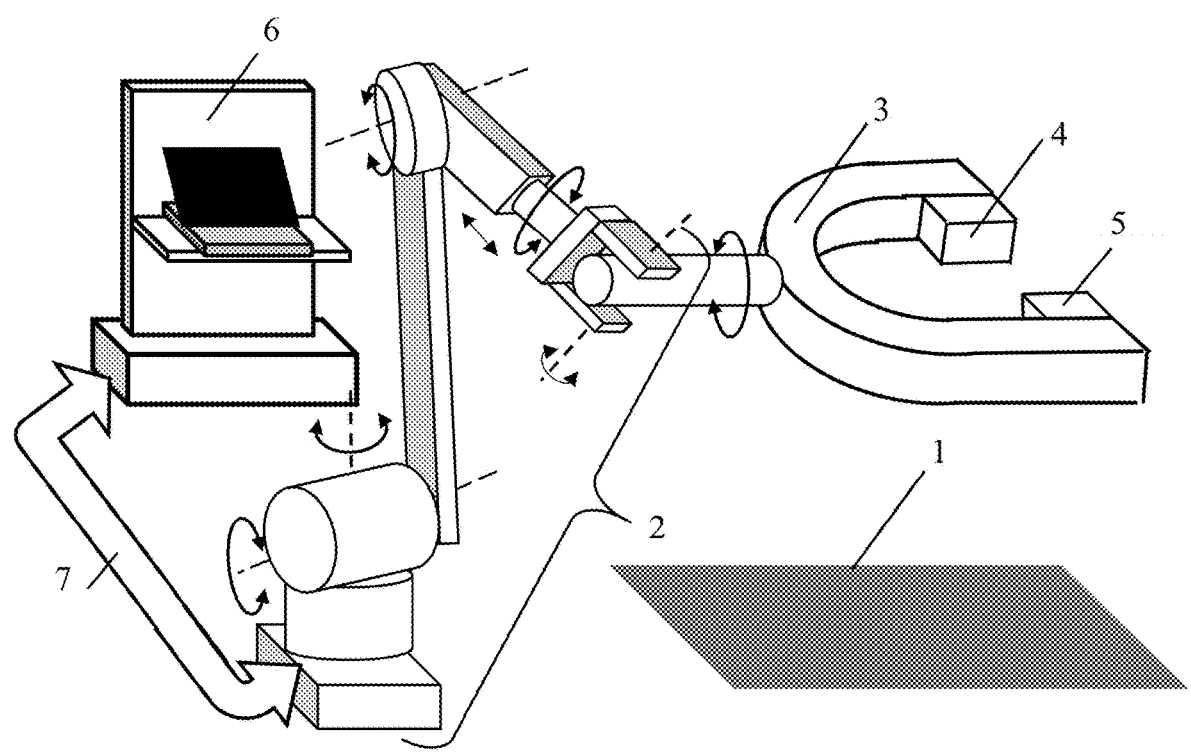
FIG. 1 schematically shows the perspective view of the tissue diffractometers based of robotic x-ray diffractometer system according to one embodiment.

Various embodiments of the invention have been shown and described herein for example purposes only. Numerous variations, changes, and substitutions are possible without departing from the invention. It should be understood that various alternatives to the embodiments of the invention described herein may be employed.

Systems and methods for providing a quantitative-diagnostic indicator for an animal are disclosed. The systems may comprise a plurality of tissue diffractometers operably coupled to a computer database over a network, where the tissue diffractometers are configured to acquire small-angle x-ray scattering and/or wide-angle x-ray scattering data for a tissue within the subject. Optionally, the tissue diffractometers may also be configured to acquire absorptive images of the tissue. The system is configured to collect and process diffraction data, image data, and/or other data pertinent to the animal using a data analytics algorithm to provide a quantitative-diagnostic indicator for the animal. The data analytics algorithm is randomly, periodically, or continually updated and refined using the data for a plurality of animals stored in the computer database. In some instances, the computer aided diagnostic indicator may comprise an indicator of the likelihood that the animal as cancer or some other disease. In some instances, the quantitative-diagnostic indicator may comprise a diagnosis that the animal has cancer or some other disease.

Whenever the phrase "at least," "greater than," or "greater than or equal to" precedes the first numerical value in a series of two or more numerical values, the phrase "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the phrase "no more than," "less than," or "less than or equal to" precedes the first numerical value in a series of two or more numerical values, the phrase "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Unless otherwise defined, all of the terms and phrases used herein have the same meaning as commonly understood by a PHOSITA, a person having ordinary skill in the art that applies to this disclosure.

As used in this specification and the appended claims, the singular forms "a", "an", and "the" include plural references unless the context clearly dictates otherwise. Any reference to "or" herein is intended to encompass "and/or" unless otherwise stated.

As used herein, the phrase "tissue diffractometer" generally refers to a diffractometer configured to record diffraction data from one or more tissues. The tissue diffractometer may be an x-ray diffractometer. In some instances, the tissue diffractometer may be configured to record diffraction data and image data.

As used herein, the term "animals" generally refers to domestic animals such as cats, dogs, rabbits, mice, rats, hamsters, guinea pigs, squirrels, chinchillas and other animals.

As used herein, the phrase "quantitative-diagnostic indicator" refers to an indicator comprising quantitative-diagnostic information that may be generated with the help of one or more computer processors. The term "quantitative" has the meaning commonly understood by a PHOSITA. To clarify one aspect of that meaning, "quantitative" as used herein means that the corresponding diagnostic indicator is information that can be understood by anyone, without the need for professional interpretation by a health professional such as a medical doctor. In some instances, the "quantitative-diagnostic indicator" may comprise a probability score for the likelihood that a subject has cancer, e.g., breast cancer. In some instances, the "quantitative-diagnostic indicator" may comprise a diagnosis that a subject has cancer, e.g., breast cancer.

As used herein, the phrase "veterinary services provider" generally refers to a veterinarian practitioner or support staff. The veterinary services provider may be a doctor, a veterinary nurse, a dentist, a technician, a student, or the like. The veterinary services provider may be at least partially responsible for the healthcare of the animal.

As used herein, the term "institution" generally refers to an entity related to one or more veterinary services providers. The institution may be a veterinary center, a veterinary office, a veterinary hospital, a university, or the like.

As used herein, the term "cancer" generally refers to a proliferative disorder caused or characterized by a proliferation of cells which have lost susceptibility to normal growth control. Cancers of the same tissue type usually originate in the same tissue and may be divided into different subtypes based on their biological characteristics. The malignant tumors (cancer) are classified according to morphological characteristics: a) epithelial (papillomas, adenomas, carcinomas, cysts, dermatomas); b) connective tissue (fibroids, myxomas, lipomas, chondromas, osteomas, melanosarcomas); c) nervous tissue (gliomas, neurinomas, meningiomas); d) muscle (fibroids, rhabdomyomas); e) vascular (hemangiomas and lymphangiomas); f) mixed (osteosarcomas and fibromyxochondroma, fibrochondroosteoma).

As used herein, the phrase "Q-beam™ x-ray diffractometer" generally refers to an x-ray diffractometer that produces a thin beam of collimated monochrome x-rays. in which the x-rays are approximately parallel and the cross-section of the beam has the form of a square. a rectangle, circle, or ellipse.

As used herein, the term "cloud" generally refers to shared or sharable storage of electronic data, e.g., a distributed network of computer servers. In some instances, the cloud may be used for archiving electronic data, sharing electronic data, and analyzing electronic data.

The methods and systems described herein are applied to characterization of tissues, e.g., soft tissues, within an animal, e.g., characterization of tissues in situ or in vivo. Examples of organs and tissues that may be characterized using the disclosed methods and systems include, but are not limited to, pancreas, mammary gland, thyroid, ovary, uterus, testis, prostate, pituitary gland, adrenal gland, kidney, stomach, esophagus, rectum, small intestine, colon, liver, gall bladder, head and neck, tongue, mouth, eye and orbit, bone, joints, brain, nervous system, skin (pelt), blood, nasopharyngeal tissue, lung, larynx, urinary tract, cervix, vagina, exocrine glands, and endocrine glands.

Diffractometer-based systems and methods of use: In one aspect, the present disclosure provides a system that outputs a quantitative-diagnostic indicator for an animal that may have or may be at risk for developing a disease, such as a proliferative disease or cancer. The system may comprise one or more tissue diffractometers operatively coupled to a computer database over a network. A tissue diffractometer of the one or more tissue diffractometers may be configured for transfer of image data, diffraction pattern data, subject data, or any combination thereof to the computer database over the network. The system may comprise one or more computer processors operatively coupled to the one or more diffractometers. The one or more computer processors may be individually or collectively configured to (i) receive the image data, diffraction pattern data, animal data, or any combination thereof from the one or more tissue diffractometers; (ii) transmit the image data, diffraction pattern data, animal data, or any combination thereof to the computer database; and (iii) process the image data, diffraction pattern data, animal data, or any combination thereof for an individual subject using a data analytics algorithm that provides a quantitative-diagnostic indicator for the individual animal.

In another aspect, the present disclosure provides a method for generating a quantitative-diagnostic indicator for a animal that may have or may be at risk for developing a disease, such as a proliferative disease or cancer. The method may comprise acquiring data comprising image data, diffraction pattern data, animal data, or any combination thereof for an individual animal using one of a plurality of tissue diffractometers operatively coupled to a computer database over a network. The plurality of tissue diffractometers may be configured for transfer of the data to the computer database over the network. One or more computer processors may be operatively coupled to the plurality of tissue diffractometers. The one or more computer processors may be used to receive the data comprising image data, diffraction pattern data, animal data, or any combination thereof from the plurality of tissue diffractometers that are operatively coupled to a computer database over the network and may be configured for transfer of the data comprising the image data, diffraction pattern data, animal data, or any combination thereof to the computer database over the network. The data comprising the image data, diffraction pattern data, animal data, or any combination thereof may be transmitted to the computer database. The data comprising the image data, diffraction pattern data, animal data, or any combination thereof may be processed for the individual subject using a data analytics algorithm that may provide a quantitative-diagnostic indicator for the individual animal. The following description may relate to both the method and the system.

In some instances, the one or more tissue diffractometers may be tissue diffractometers as described elsewhere herein. The one or more tissue diffractometers may be stand-alone tissue diffractometers (e.g., instruments or components of a system that do not comprise other functionalities). The one or more tissue diffractometers may be coupled with other instruments. The operative coupling to a computer database may be over a local network (e.g., a local area network (LAN)) or a remote network (e.g., the internet).

In some instances, the image data may be images, image metadata, or the like, or any combination thereof. The images may be raw images (e.g., images as captured from a detector), processed images (e.g., images that have had one or more processing operations performed), image analogues (e.g., matrices of intensity values corresponding to pixels, vector representations of images), or the like. The image metadata may comprise non-image information regarding the conditions at which the image was acquired (e.g., x-ray wavelength, detector distance from the source and/or the sample, exposure time, date and time of acquisition, ambient conditions, etc.).

In some instances, the diffraction pattern data may comprise diffraction patterns, diffraction pattern metadata, or the like, or any combination thereof. The diffraction patterns may comprise diffraction patterns generated from an interaction of a radiation beam (e.g., an x-ray beam, a neutron beam) with a tissue. The diffraction patterns may comprise raw diffraction patterns, processed diffraction patterns, diffraction pattern analogues, or the like. The diffraction pattern metadata may comprise metadata as described elsewhere herein.

In some instances, the image data and/or diffraction pattern data may comprise data taken from both a healthy tissue and a tissue suspected of having an abnormality. Both the healthy tissue and the tissue suspected of having an abnormality may be of a same animal.

In some instances, the animal data may comprise an animal's age, sex, weight, body condition score (BCS), ancestry data, genetic data, behavioral data, medical history, previous veterinary tests or diagnostics, or any combination thereof. The ancestry data may be determined by one or more genetic tests. The ancestry data may comprise ancestry data reported by the animal owner. The genetic data may comprise genetic abnormalities, predispositions, or the like. For example, the animal data may comprise information regarding an animal's genetic predisposition to breast cancer (e.g., the presence or absence of a breast cancer gene).

In some instances, the computer database may be a cloud-based database, e.g., a database that resides on one more remote computer servers. In some instances, the computer database may be a local computer database (e.g., a computer connected to a tissue diffractometer).

In some instances, the one or more computer processors may be computer processors that are part of one or more computer servers that host the computer database. In some instances, the one or more computer processors may be computers operatively coupled to the one or more tissue diffractometers (e.g., computers controlling the one or more diffractometers). The receiving of image data may comprise real-time or substantially real-time receipt of the image data. For example, in some instances, a stream of image data can be transmitted from a tissue diffractometer to the one or more computer processors as the images are being taken. In some instances, the image data may be transmitted in packets (e.g., bundles of one or more images). For example, a series of images of a plurality of animals can be taken throughout a day and can then be all transmitted together. In another example, all images taken of a single subject during a single scan or single session can be transmitted together. The transmitting to the computer database may be real-time transmitting, substantially real-time transmitting, intermittent transmitting (e.g., transmitting packets), or any combination thereof.

In some instances, diffraction data processing and/or image data processing may occur between the receiving of the diffraction and/or image data and the transmitting of image data. For example, in some instances, the one or more computer processors may be configured to compress the diffraction and/or image data to improve the transfer speed to the database. In another example, the one or more computer processors can be configured to extract relevant parameters (e.g., d spacings, pair distribution functions) from the data (e.g., diffraction pattern data) before transmitting to the computer database, thereby significantly decreasing the amount of data to be transmitted. In some instances, the processing of diffraction and/or image data may be performed after the data has been transferred to the computer database. The processing of the diffraction and/or image data may be local processing (e.g., processing on a computer local to the tissue diffractometers) or remote processing (e.g., processing on a remote computer server or cloud-based server). In some instances, the data processing may comprise the application of a statistical analysis and/or machine learning algorithm (which individually or collectively may be referred to as a "data analytics algorithm" herein). The data processing may comprise processing diffraction data and/or image data for a single subject or a plurality of subjects. For example, the diffraction and/or image data acquired for a single animal can be processed to generate the quantitative-diagnostic indicator for the animal. In another example, diffraction data and/or image data from a plurality of subjects may be processed to refine the data analytics algorithm and/or to generate a baseline diagnostic indicator.

In some instances, the system may further comprise a user interface. The user interface may be configured to allow an individual animal owner and/or their veterinary services provider to upload the individual animal's image data, diffraction pattern data, subject data, or any combination thereof to the computer database. The uploading the individual animal's image data, diffraction pattern data, animal data, or any combination thereof to the computer database may be in exchange for processing the individual animal's image data, diffraction patter data, or any combination thereof to receive the quantitative-diagnostic indicator for the individual animal. The user interface may be configured to allow an individual animal owner and/or their veterinary services provider to make payments and/or upload the individual consent form signed by animal owner. The payments may be cash payments (e.g., the user interface displays an address to send the payments), check payments (e.g., paper or electronic check payments), card payments (e.g., credit or debit card payment processing), app-based payments (e.g., PayPal®, Venmo®), cryptocurrency payments (e.g., Bitcoin), or any combination thereof. The signed consent form may be signed by the individual animal owner and/or the veterinary services provider. The signed consent form may be related to the quantitative-diagnostic indicator. For example, the individual animal owner can sign and upload a consent form stating that the subject's diffraction and/or image data may be retained on the computer database. In some instances, the signed consent form may be physically signed, electronically signed, or any combination thereof.

In some instances, a system of the present disclosure may comprise 1, 2, 3, 4, 5, 6, 7, 8, 9, 10, 20, 30, 40, 50, 60, 70, 80, 90, 100, 150, 200, 250, 300, 350, 400, 450, 500, or more than 500 tissue diffractometers. In some instances, a system of the present disclosure may comprise at most about 500, 450, 400, 350, 300, 250, 200, 150, 100, 90, 80, 70, 60, 50, 40, 30, 20, 10, 9, 8, 7, 6, 5, 4, 3, 2, or fewer than 2 tissue diffractometers. In some instances, the number of tissue diffractometers in the system may range between any two of the values specified in this paragraph. For example, in some instances, the number of tissue diffractometers in the system may range from 4 to 100. Those of skill in the art will recognize that in some instances, the number of tissue diffractometers in the system may have any value within the range of values specified in this paragraph, e.g., 125 tissue diffractometers.

The one or more tissue diffractometers may be two or more tissue diffractometers located in two or more different geographic locations. For example, a first tissue diffractometer in a first location can send one set of image data to the one or more computer processors while a second tissue diffractometer in a second location can send one set of diffraction pattern data to the one or more computer processors. In this example, the image data and the diffraction pattern data can both be used to refine the data analytics algorithm that generates quantitative-diagnostic indicators for individual animals, and may also both be retained on the computer database. The one or more tissue diffractometers may comprise a data encryption device. The data encryption device may comprise a global positioning system (GPS) positioning sensor. The data encryption device may generate encrypted image data, diffraction pattern data, animal data, or any combination thereof. The encrypted image data, diffraction pattern data, animal data, or any combination thereof may be transferred to the computer database. The encrypted image data, diffraction pattern data, animal data, or any combination thereof may comprise data regarding changes in a location of the one or more tissue diffractometers. For example, the image metadata generated by a tissue diffractometer can comprise location information for that tissue diffractometer. In this example, a movement of the tissue diffractometer can be tracked using the image metadata transmitted by the tissue diffractometer. In another example, the GPS positioning sensor can be in constant communication with the computer database regarding the location of the tissue diffractometer. The inclusion of the GPS sensor may reduce a likelihood that the tissue diffractometer is stolen or misappropriated by untrained users. The data encryption device may comprise a module configured to only permit communication between the tissue diffractometer and the computer database. For example, other network communications can be disabled such that the data from the tissue diffractometer can be sent only to the computer database.

In some instances, the plurality of tissue diffractometers that are operatively coupled to the system may be located in 2, 3, 4, 5, 6, 7, 8, 9, 10, 20, 30, 40, 50, 60, 70, 80, 90, 100, 150, 200, 250, 300, 350, 400, 450, 500, or more than 500 different geographical locations (thereby effectively constituting a global diagnostic system). In some instances, the number of different geographical locations comprising tissue diffractometers that are operatively coupled to the system may range between any two of the values specified in this paragraph. For example, in some instances, the number of different geographical locations included in the system may range from 8 to 20. Those of skill in the art will recognize that in some instances, the number of different geographical locations included in the system may have any value within the range of values specified in this paragraph, e.g., 14 different geographical locations.

Small angle x-ray scattering: In some instances, the one or more tissue diffractometers may be configured to perform small angle x-ray scattering (SAXS) measurements. The SAXS measurements may comprise measurements of the long-range ordering of the tissue. For example, the SAXS measurement can record measurements of tissue order in the range of 10 to 1,000 nanometers. The SAXS measurements may comprise measurements of scattering of at least about 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.6, 7, 7.5, 8, 8.5, 9, 9.5, 10, or more degrees. The SAXS measurements may comprise measurements of at most about 10, 9.5, 9, 8.5, 8, 7.5, 7, 6.5, 6, 5.5, 5, 4.5, 4, 3.5, 3, 2.5, 2, 1.5, 1, 0.9, 0.8, 0.7, 0.6, 0.5, 0.4, 0.3, 0.2, 0.1, 0.05, 0.01, or less degrees. The SAXS measurements may comprise measurements of a range as defined by any two of the proceeding numbers. For example, the SAXS measurements may comprise measurements of scattering of 0.1-10 degrees. The SAXS measurements may comprise measurements with respect to degrees (e.g., $\Theta$), $2\Theta$, d (e.g., distance measured in Angstroms), q (e.g., 1/d), or the like, or any combination thereof.

Wide angle x-ray scattering: In some instances, the one or more tissue diffractometers may be configured to perform wide angle x-ray scattering (WAXS) measurements. The WAXS measurements may comprise measurements of the short-range ordering of the tissue. For example, the WAXS measurements can record measurements of the tissue order below 10 nanometers. The WAXS measurements may provide structural information about non-tissue objects in the tissue. For example, a WAXS measurement of an object suspected of being a breast calcification can confirm that the object is composed of calcium oxalate and calcium phosphate. In another example, a WAXS measurement can generate information regarding a molecular structure within a tissue. The WAXS measurements may comprise measurements of at least about 10, 15, 20, 25, 30, 35, 40, 45, or more degrees. The WAXS measurements may comprise measurements of at most about 45, 40, 35, 30, 25, 20, 15, 10, or less degrees. The WAXS measurements may comprise measurements of a range as defined by any two of the proceeding numbers. For example, the WAXS measurements can comprise measurements of scattering of 10-45 degrees. The WAXS measurements may comprise measurements with respect to degrees (e.g., $\Theta$), $2\Theta$, d (e.g., distance measured in Angstroms), q (e.g., 1/d), or the like, or any combination thereof.

Computer database: As noted above, in some instances, the computer database may reside on a central computer server. In some instances, the central computer server may reside in the cloud (e.g., may be a cloud-based computer server comprising a distributed network of remote computer servers). In some instances, the computer database may reside on a local server. In some instances, data may be transferred or exchanged between a local computer database and a remote or central computer database. The computer database may reside on a privacy law compliant server (e.g., a HIPAA complaint server).

Data analytics algorithm: As noted above, in some instances the data analytics algorithm may comprise a statistical analysis of diffraction pattern data and/or a function thereof. In some instances, the data analytics algorithms may comprise a statistical analysis of image data, diffraction pattern data, animal data, a function of any of the proceeding, or any combination thereof. In some instances, the statistical analysis may comprise determination of a pairwise distance distribution function, determination of a Patterson function, a calculation of a Porod invariant, Fourier transformation and calculation of pair-wise distance distribution function, a cluster analysis, a dispersion analysis, determination of one or more molecular structural periodicities, or any combination thereof. The statistical analysis may comprise a determination of a structural periodicity of a tissue or a tissue feature. The structural analysis may comprise a determination of a structural periodicity of collagen, one or more lipids, or a combination thereof. For example, a diffraction pattern can provide information regarding the structural periodicity, and thus the relative degree of ordering, of the collagen within the spot size of the diffractometer. In another example, the ordering of lipid layers can be determined by diffraction, which can give information about the stiffness of the lipid layers and the chemical composition of the layers (e.g., the amount of cholesterol or other stiffening agents) on a local level. In some instances, the structural periodicity of the tissue may be used to determine a likelihood of a cancer being present within the tissue. For example, the collagen in the normal tissue is more well-structured, which can give rise to stronger diffraction peaks, while the collagen in the carcinoma is poorly structured, which can result in weak diffraction peaks.

In some instances, the data analytics algorithm may comprise or further comprise the use of one or more machine learning algorithms. The one or more machine learning algorithms may be configured to operate upon image data, diffraction pattern data, animal data, or any combination thereof. The machine learning algorithm may comprise one or more supervised learning algorithms, one or more unsupervised learning algorithms, one or more semi-supervised learning algorithms, one or more reinforcement learning algorithms, one or more deep learning algorithms, or any combination thereof. The machine learning algorithm may be a deep learning algorithm. The deep learning algorithm may comprise one or more convolutional neural networks, one or more recurrent neural networks, and/or one or more recurrent convolutional neural networks.

Statistical analysis algorithms and/or machine learning algorithms implemented on a local computer or a remote server may be used to perform data analytics. For example, a machine learning algorithm can be configured to pre-process raw image data, diffraction pattern data, and/or animal data to remove noise or other artifacts. A different machine learning can be trained to identify features within the image data, diffraction pattern data, and/or animal data. Such a machine learning algorithm can cluster data points for use as an identification algorithm. Other machine learning algorithms can be configured to provide a quantitative-diagnostic indicator.

The machine learning algorithms may comprise a supervised, semi-supervised, or unsupervised machine learning algorithm. A supervised machine learning algorithm, for example, is an algorithm that is trained using labeled training data sets, e.g., data sets that comprise training inputs with known outputs. The training inputs can be provided to an untrained or partially trained version of the machine learning algorithm to generate a predicted output. The predicted output can be compared to the known output in an iterative process, and if there is a difference, the parameters of the machine learning algorithm can be updated. A semi-supervised machine learning algorithm is trained using a large set of unlabeled training data, e.g., unlabeled training inputs, and a small number of labeled training inputs. An unsupervised machine learning algorithm, e.g., a clustering algorithm, may find previously unknown patterns in data sets comprising data with no pre-existing labels.

One non-limiting example of a machine learning algorithm that can be used to perform some of the functions described above, e.g., processing of diffraction data, animal data, and/or generating quantitative-diagnostic indicators, is a neural network. Neural networks employ multiple layers of operations to predict one or more outputs, e.g., a likelihood that a subject has cancer, from one or more inputs, e.g., image data, diffraction pattern data, animal data, processed data derived from image data, diffraction pattern data, and/or animal data, or any combination thereof. Neural networks can include one or more hidden layers situated between an input layer and an output layer. The output of each layer can be used as input to another layer, e.g., the next hidden layer or the output layer. Each layer of a neural network can specify one or more transformation operations to be performed on the data input to the layer. Such transformation operations may be referred to as "neurons". The output of a particular neuron may be, for example, a weighted sum of the inputs to the neuron, that is optionally adjusted with a bias and/or multiplied by an activation function, e.g., a rectified linear unit (ReLU) or a sigmoid function.

Training a neural network can involve providing inputs to the untrained neural network to generate predicted outputs, comparing the predicted outputs to expected outputs, and updating the algorithm's weights and biases in an iterative manner to account for the difference between the predicted outputs and the expected outputs. For example, a cost function can be used to calculate a difference between the predicted outputs and the expected outputs. By computing the derivative of the cost function with respect to the weights and biases of the network, the weights and biases can be iteratively adjusted over multiple cycles to minimize the cost function. Training may be complete when the predicted outputs satisfy a convergence condition, such as obtaining a small magnitude of calculated cost.

Convolutional neural networks (CNNs) and recurrent neural networks can be used to classify or make predictions from image data, diffraction pattern data, animal data, or any combination thereof. CNNs are neural networks in which neurons in some layers, called convolutional layers, receive data from only small portions of a data set. These small portions may be referred to as the neurons' receptive fields. Each neuron in such a convolutional layer may have the same weights. In this way, the convolutional layer can detect features, e.g., cancerous growths, in any portion of the input image data, diffraction data, or a combination thereof.

RNNs, meanwhile, are neural networks with cyclical connections that can encode dependencies in time-series data, e.g., longitudinal study images of one or more animals. An RNN may include an input layer that is configured to receive a sequence of time-series inputs, e.g., image data, diffraction pattern data, animal data, or any combination thereof collected over a period of time. An RNN may also include one or more hidden recurrent layers that maintain a state. At each time step, each hidden recurrent layer can compute an output and a next state for the layer. The next state can depend on the previous state and the current input. The state can be maintained across time steps and can capture dependencies in the input sequence. Such an RNN can be used to determine time-series features or evolutions of features within the animal data.

One example of an RNN is a long short-term memory network (LSTM), which can be made of LSTM units. An LSTM unit can be made of a cell, an input gate, an output gate, and a forget gate. The cell can be responsible for keeping track of the dependencies between the elements in the input sequence. The input gate can control the extent to which a new value flows into the cell, the forget gate can control the extent to which a value remains in the cell, and the output gate can control the extent to which the value in the cell is used to compute the output activation of the LSTM unit. The activation function of the LSTM gate may be, for example, the logistic function.

Other examples of machine learning algorithms that can be used to process image data, diffraction pattern data, animal data, or any combination thereof are regression algorithms, decision trees, support vector machines, Bayesian networks, clustering algorithms, reinforcement learning algorithms, and the like.

The clustering algorithm may be, for example, a hierarchical clustering algorithm. A hierarchical clustering algorithm can be a clustering algorithm that clusters animals based on their proximity to other animals. For example, a hierarchical clustering algorithm can cluster image data, diffraction pattern data, animal data, or any combination thereof. The clustering algorithm can alternatively be a centroid-based clustering algorithm, e.g., a k-means clustering algorithm. A k-means clustering algorithm can partition n observations into k clusters, where each observation belongs to the cluster with the nearest mean. The mean can serve as a prototype for the cluster. In the context of image data, diffraction pattern data, animal data, or any combination thereof, a k-means clustering algorithm can generate distinct groups of data that are correlated with each other. Thereafter, each group of data can be associated with, e.g., a particular probability or diagnosis of cancer, based on knowledge about that subsystem, e.g., knowledge about previous diagnoses and data. The clustering algorithm can alternatively be a distribution-based clustering algorithm, e.g., a Gaussian mixture model or expectation maximization algorithm. Examples of other clustering algorithms are cosine similarity algorithms, topological data analysis algorithms, and hierarchical density-based clustering of applications with noise (HDB-SCAN).

The machine learning algorithm may be trained using a training dataset comprising image data, diffraction pattern data, subject data, or any combination thereof. The training dataset may be stored in the computer database for a specific pathology and/or physiological norm group. The training dataset may be obtained using the one or more tissue diffractometers. The training dataset may comprise information regarding a confirmation of a diagnosis for given set of data. For example, data comprising a plurality of images and diffraction patterns of a tissue suspected of being cancerous can also comprise a histological confirmation of the presence of the cancer in the tissue. A set of diffraction images can be accompanied by data regarding the longevity of the subject that the diffraction images were taken from. The computer database for the specific pathology and/or physiological norm group may be a remote computer database (e.g., a cloud-based database) or a local database (e.g., a computer system local to a tissue diffractometer). For example, the training dataset for breast cancer diagnostic indicators can be stored on a computer database with other breast cancer diagnostic data. The training dataset may be updated as new image data, diffraction pattern data, subject data, or any combination thereof is uploaded to the computer database. The updating may be an inclusion of the new data, a removal of the old data, or a combination thereof. For example, new image data can be added to the training dataset as it is taken to improve the quality of the training dataset. In another example, poor quality data may be removed from the training dataset when higher quality new data is added. The statistical analysis algorithm and/or machine learning algorithm (e.g., the data analytics algorithm) may be updated when the computer database or training dataset residing thereon is updated. For example, a machine learning algorithm can be retrained using the new training dataset to improve the efficacy of the machine learning algorithm in generating a quantitative-diagnostic indicator. The statistical analysis and/or machine learning algorithm may be continuously, periodically, or randomly updated and refined as the training dataset is updated. In this example, the revised statistical analysis and/or machine learning algorithm may be more accurate, specific, and/or sensitive in providing a probability or diagnosis than a previous version derived from a previous training dataset was.

Quantitative-diagnostic indicator: In some instances, the quantitative-diagnostic indicator for the individual animal may comprise an indicator of a likelihood that the individual animal has a cancer or other disease. The quantitative-diagnostic indicator for the individual animal may comprise an indicator of a likelihood that the individual animal has breast cancer. For example, a quantitative-diagnostic indicator can comprise a banded risk assessment for the individual animal (e.g., high risk, medium risk, low risk). The quantitative-diagnostic indicator may be displayed on a user interface of a device (e.g., a user interface on a computer screen, a user interface on a tablet). The quantitative-diagnostic indicator may be a report. The report may be a printed report. The report may comprise additional information. For example, the report may comprise a likelihood of the animal having a cancer, as well as the indicators that contributed to the generation of the report and a suggestion of possible next steps for the animal to take. The indicator may be a percentage (e.g., a percentage likelihood that the animal has the cancer), a risk band (e.g., high risk, medium risk, low risk), a comparison of factors (e.g., a list of factor indication a presence and a list of factors indicating an absence), or the like, or any combination thereof. The indicator of the likelihood that the individual animal has cancer may be an indicator of the likelihood that the individual animal has breast cancer.

By way of example, and not by way of limitation, the embodiment depicted in FIG. 1, schematically shows a perspective view of the invented tissue diffractometer, comprising an animal positioning area (1), a robotic arm (2) having a C-arc (3) with a source for producing Q-beam™ x-ray beams (4) and an x-ray detector (5) for detection of x-rays passing through animal tissue and scattered by it which are mounted onto the C-arc opposite each other, a computer work-station (6) and a means of communication (7) of the computer work-station with robotic x-ray diffractometer system.

Figure 2A:
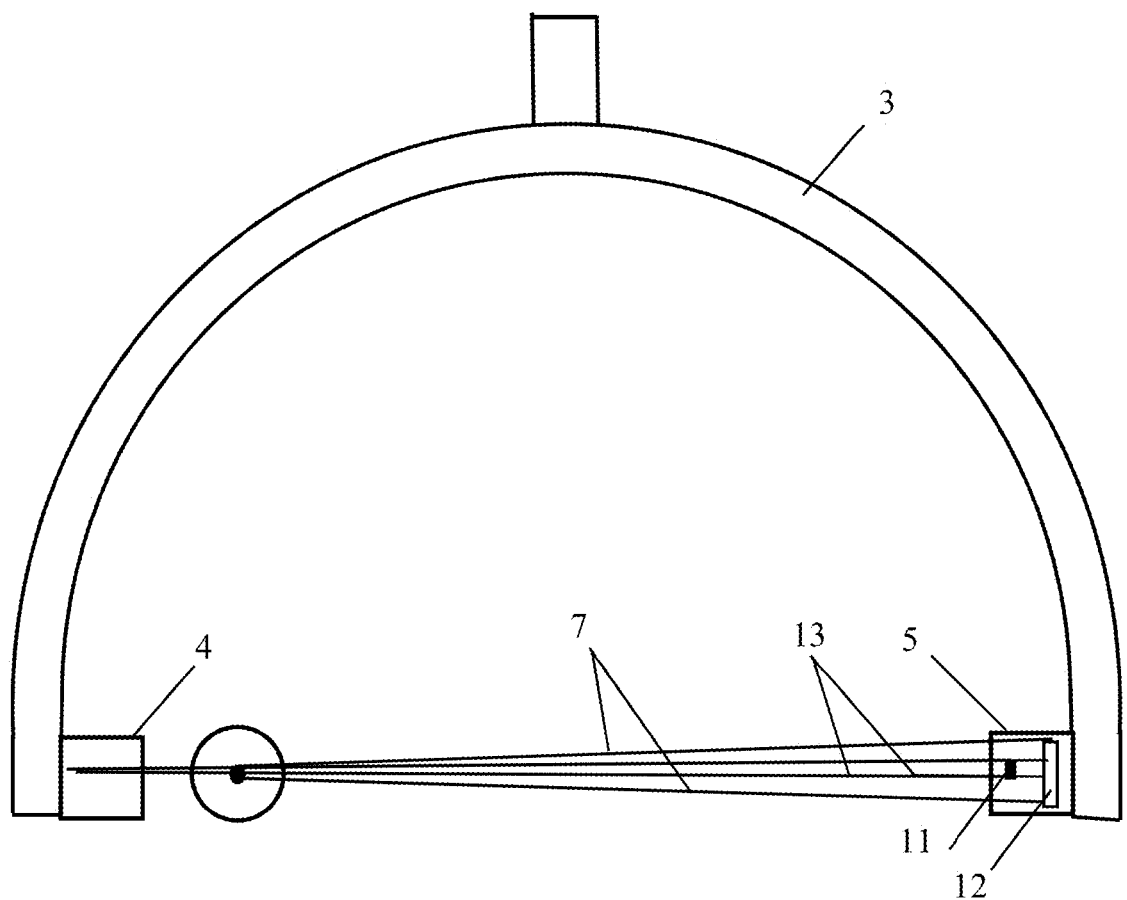
FIGS. 2a-2c schematically show x-ray apparatus located onto the C-arc.
Figure 2B:
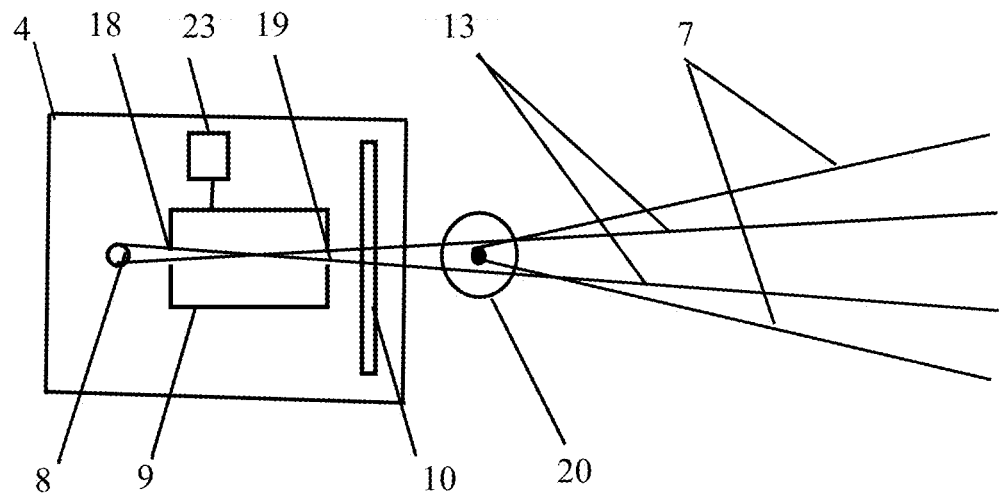
Figure 2C:
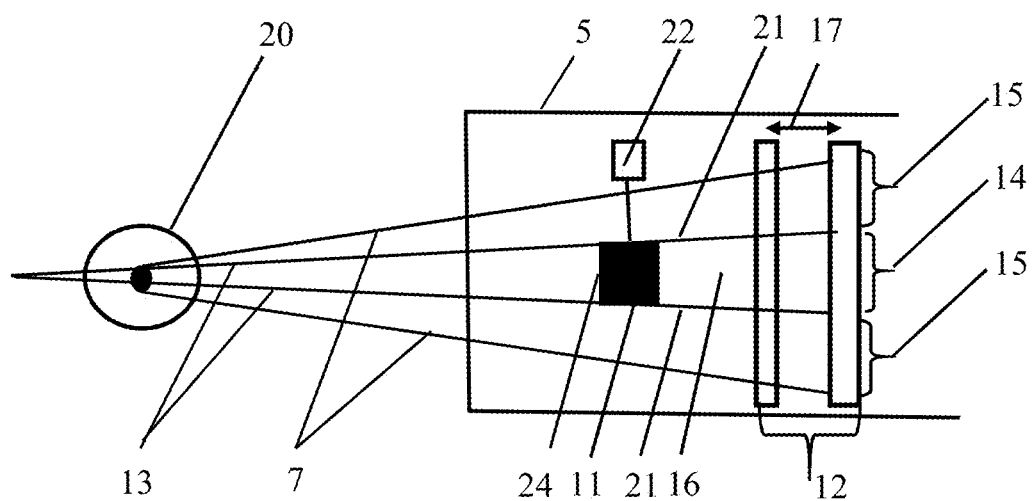

FIGS. 2*a*-2*c* schematically show x-ray apparatus located onto the C-arc (3). The source of the Q-beam™ x-ray beams (4) comprises radiation source (8), a beam forming apparatus (9), an adjustable diaphragm (10) and the receiver (5) of the collimated x-ray comprises a filter (11) and a two dimensional detector (12). In operation, the beam forming apparatus (9) forms the radiation into a weakly diverging incident beam (13). FIGS. 2a-2c schematically show x-ray beams (7) scattered by the animal tissue (20). A suitable beam forming apparatus (9) includes, but is not limited to, a Kratki or Montel mirror collimator. The incident beam (13) passes from the beam forming apparatus (9) through the animal tissue (20) to the detector (12). The detector (12) receives radiation in a transmitted beam zone (14) and a scattering zone (15). The transmitted beam zone (14) receives the transmitted beam (16) and the scattering zone (15) receives radiation scattered outside the transmitted beam (16) by the animal tissue (20). A surface (24) of the filter (11) facing the source of collimated x-ray has a shape matching the shape of the cross section of the transmitted beam (16). The filter (11) can be removable positioned in the transmitted beam (16) such that the dimensions of the surface (24) is matched to the outer edges (21) of the transmitted beam (16). Suitable materials for the filter (11) include, but are not limited to, leaded glass or metals such as invar which changes shape minimally with changing temperatures. The lateral surface of the of the filter (11) are optically polished to form a sharp upper edge on the filter (11). The filter (11) screens the transmitted beam zone (14) from the transmitted beam (16). This screen will cause only scattered radiation which has passed out of the transmitted beam (16) before reaching the filter (11) to be received by the scattering zone (15). The filter (11) can be mechanically moved into the transmitted beam (16) with a micro-motor (22). Suitable micro-motors (22) include, but are not limited to high precision piezo-ceramic motors.

The detector (12) position adjuster moves the detector (12) relative to the animal tissue (20) as illustrated by the arrow (17). The drive train for the position adjuster can be similar to the drive train used to adjust the height of optics assemblies in photocopiers. Movement of the detector (12) relative to the animal tissue (20) changes the resolution of the detector (12) toward radiation scattered over certain angles. For instance, moving the detector (12) further from the animal tissue (20) increases the area of the detector (12) exposed to radiation scattered over small angles. The larger the detector (12) area exposed to radiation scattered over certain angles, the higher the resolution of the detector (12) with respect to those angles. The detector (12) should be positioned to achieve the desired resolution within the angles of interest. To study radiation scattered over small angles, the detector (12) is preferably positioned approximately 1 meter from the animal tissue position (20). A distance of 1 m allows radiation scattered over small angles to exit the transmitted beam (16) before being received by the detector (12). For instance, radiation scattered from 1 arc second within the animal tissue (20) will be scattered over 300 µm from the center of the transmitted beam (16) when the detector (12) is 1 m from the animal tissue position (20).

The beam forming apparatus (9) can include a first slot shaped aperture (18) and a second slot shaped aperture (19). The width of the incident beam (13) can be adjusted by altering the size of the first and second slot shaped apertures (18), (19). A first side of the beam forming apparatus (9) is fixed while a second side of the beam forming apparatus (9) is mobile. Movement of the second side toward the first side reduces the width of the first and second slot shaped apertures (18), (19) and accordingly, the width of the incident beam (13). Narrowing the width of the incident beam (13) reduces the size of the analysis section but will achieve a higher resolution of the analysis section. Suitable widths for the first and second slot shaped apertures (18), (19) include, but are not limited to 20-120 µm, 40-80 µm and 55-65 µm. The movement of the second side toward the first side can be driven by a micromotor (23).

Figure 3:
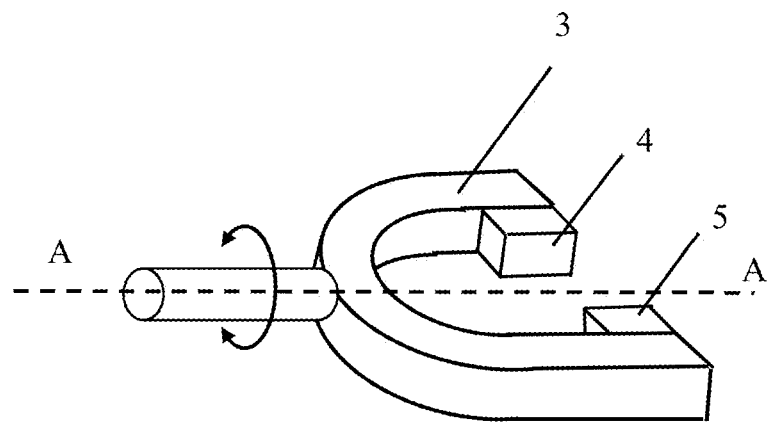
FIG. 3 schematically shows the rotation of the C-arc around its axis of symmetry.
Figure 4:
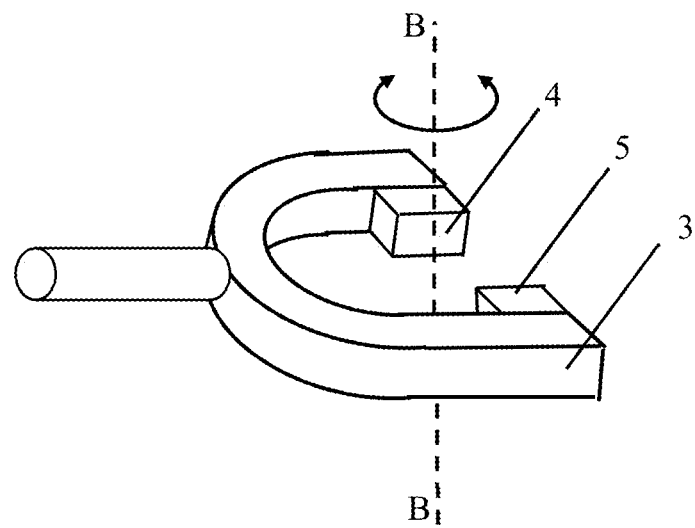
FIG. 4 schematically shows the iso-centrically rotation of the C-arc around an arbitrarily selected rotation axis perpendicular to the C-arc plane.

FIG. 3 schematically shows the rotation of the C-arc around its axis of symmetry (A-A). FIG. 4 schematically shows the iso-centrically rotation of the C-arc around an arbitrarily selected rotation axis perpendicular to the C-arc plane (B-B).

Figure 5:
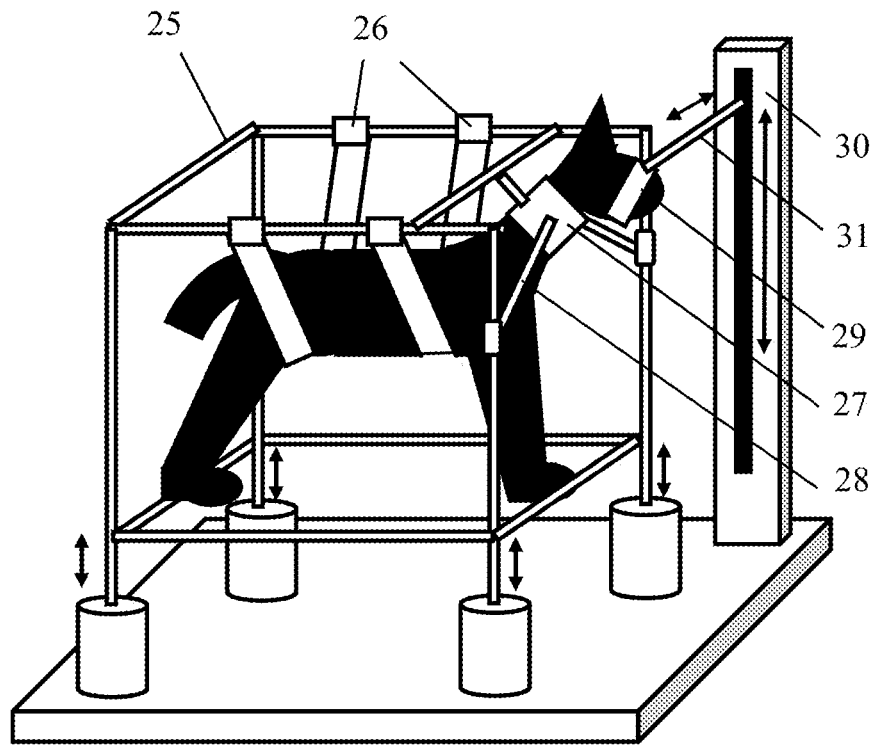
FIG. 5 schematically shows a holding device for an animal.

FIG. 5 schematically shows a gentle holding (restraining) device (25) for an animal which allows you to fix the position of the animal without the use of sedatives or anesthesia. The animal is supported in a fixed position by means of straps (26). To fix the animal's neck, a collar (27) and holding straps (28) are used. For some studies, it is necessary that the animal's head is motionless. For this purpose, a muzzle (29) and a device for fixing it (30) are used, in which the holder (31) is able to move in the vertical and horizontal direction (as indicated by the arrows).

Figure 6A:
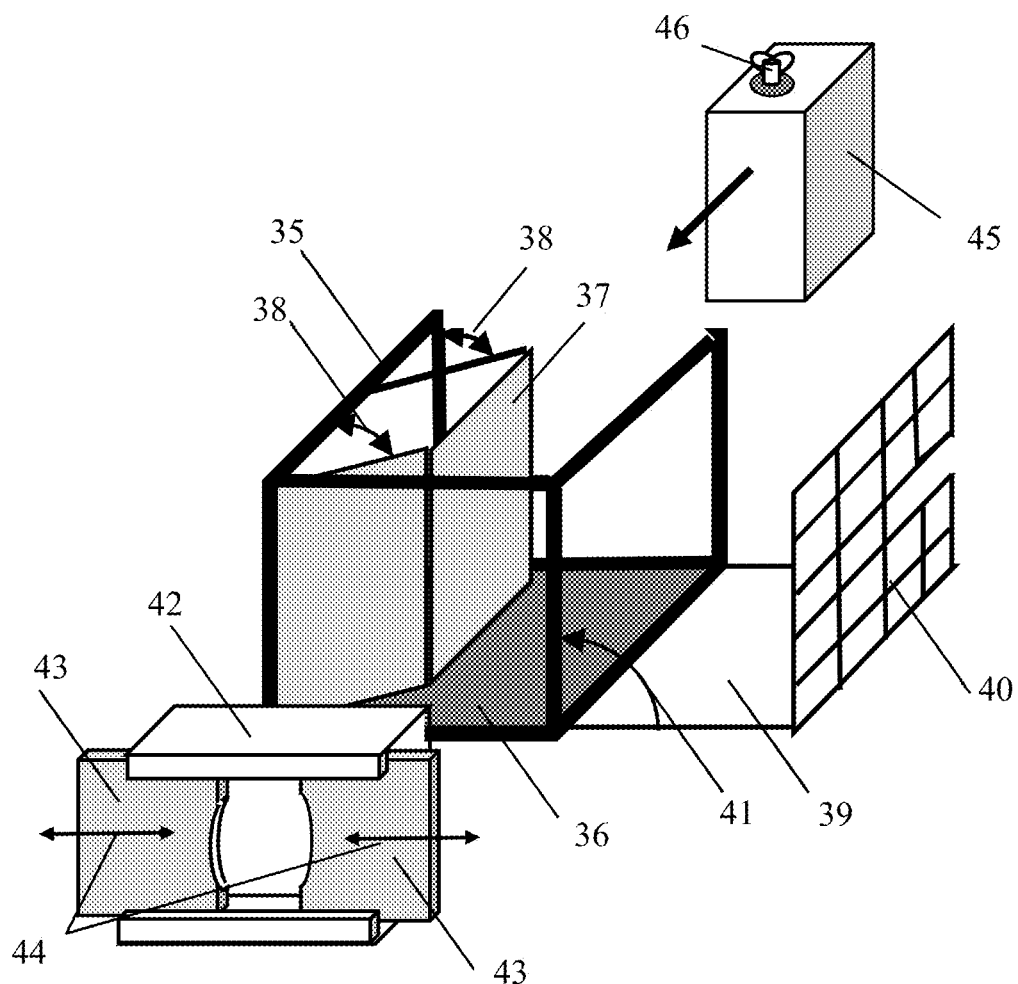
FIGS. 6a-6c schematically shows a restraint device for small-sized pets (for example, cats).
Figure 6B:
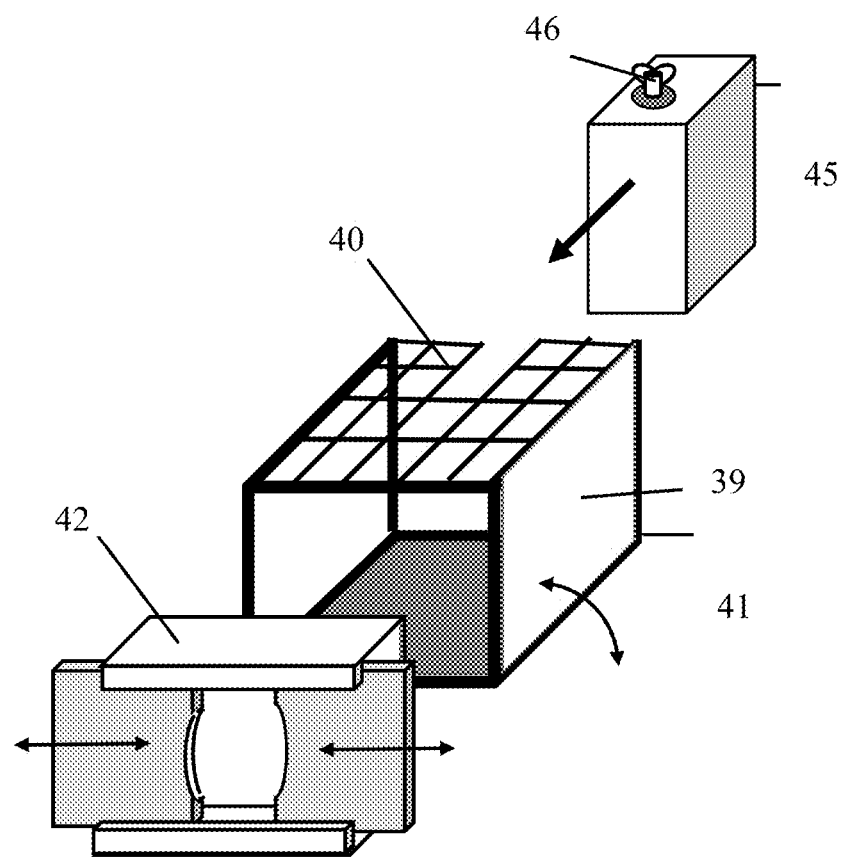
Figure 6C:
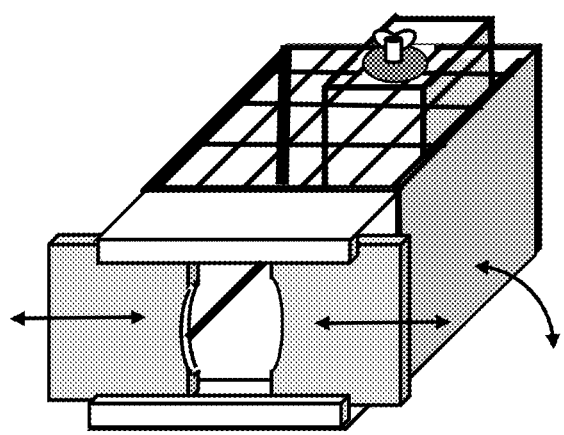

FIGS. 6a-6c schematically show a restraint device for small-sized pets (for example, cats). This device is made of materials that are transparent to x-ray radiation. The device comprises an animal positioning area (36), a supporting frame (35) on which a rotating side wall (39) and a cover transparent to visible light (40) are mounted, and a pressure wall (37) designed to immobilize the animal. The rotation of the wall (39) and the cover (40) is shown by the arrow (41) and the shift of the pressure wall is shown by the arrows (38). The movement of the pressure wall (37) can be carried out manually. The restraint device contains a block (42) designed to fix the animal's head with the help of movable shutters (43) as indicated by the arrows (44). The movement of the shutters can be carried out manually. The device element (45) is designed to limit the space behind the animal and is attached to the cover with a fixation device (46). All moving parts of the device are fixed in the established positions using fixing devices known in the technique, which are not shown in the FIGS. 6a-6c. FIGS. 6a and 6b show the device in the disassembled state, which is convenient for understanding the details of the device design, and FIG. 6c shows the device assembled.

Figure 7:
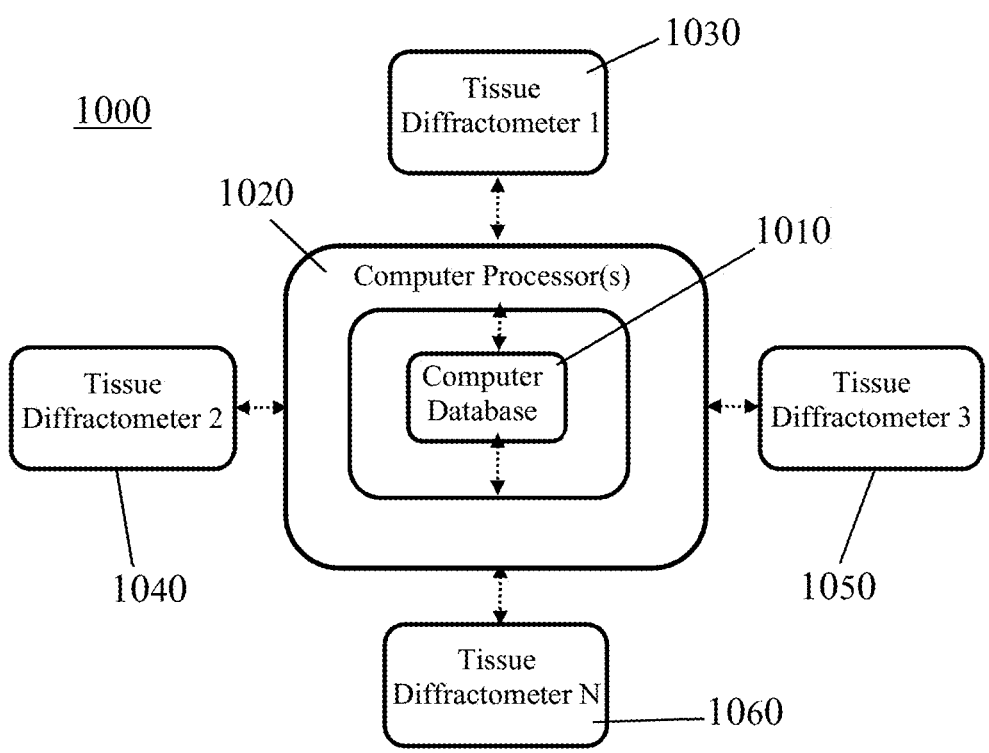
FIG. 7 shows a schematic of a plurality of tissue diffractometers operatively coupled to a computer database over a network.

FIG. 7 shows a schematic of a plurality of tissue diffractometers operatively coupled to a computer database over a network. The plurality of tissue diffractometers operatively coupled to the computer database over the network may be a global diagnostics system 1000. The global diagnostics system may comprise a computer database 1010. The computer database may be configured to store data (e.g., image data, diffraction pattern data, animal data, or any combination thereof). The central computer database may be encrypted. The computer database may be configured for compliance with health data privacy laws and regulations (e.g., HIPAA). The computer database may be a distributed computer database (e.g., a cloud-based database housed at a plurality of locations). The computer database may be configured to accept data from one or more tissue diffractometers 1030, 1040, 1050, and/or 1060 via one or more computer processor(s) 1020. The one or more computer processors may be configured to pre-process, process, and/or post-process the data as described elsewhere herein. The one or more computer processors may be coupled to the one or more tissue diffractometers via a network (e.g., a local network, the internet, a virtual private network). The one or more tissue diffractometers may be at least about 1, 5, 10, 25, 50, 75, 100, 250, 500, 750, 1,000, 2,500, 5,000, 10,000, 50,000, 100,000 or more tissue diffractometers. The one or more tissue diffractometers may be at most about 100,000, 50,000, 10,000, 5,000, 2,500, 1,000, 750, 500, 250, 100, 75, 50, 25, 10, 5, or less tissue diffractometers. The one or more tissue diffractometers may be one or more of a same type of tissue diffractometer (e.g., a same model), or one or more of a different type of tissue diffractometers (e.g., one or more different models of tissue diffractometers). The computer processors 1020 may be configured to periodically refine and update a statistical and/or machine learning based data analytics algorithm using data stored in the computer database 1010. For example, the data analytics algorithm may be updated every month, every week, every day, or every hour. In some instances, the computer processors 1020 and computer database 1010 may be configured to continually refine a statistical and/or machine learning based data analytics algorithm. For example, each time new data is received from a tissue diffractometer, the computer processors 1020 can access that new data from the computer database 1010 to update the data analytics algorithm. The data analytics algorithm may be a data analytics algorithm and/or machine learning algorithm as described elsewhere herein.

Figure 8:
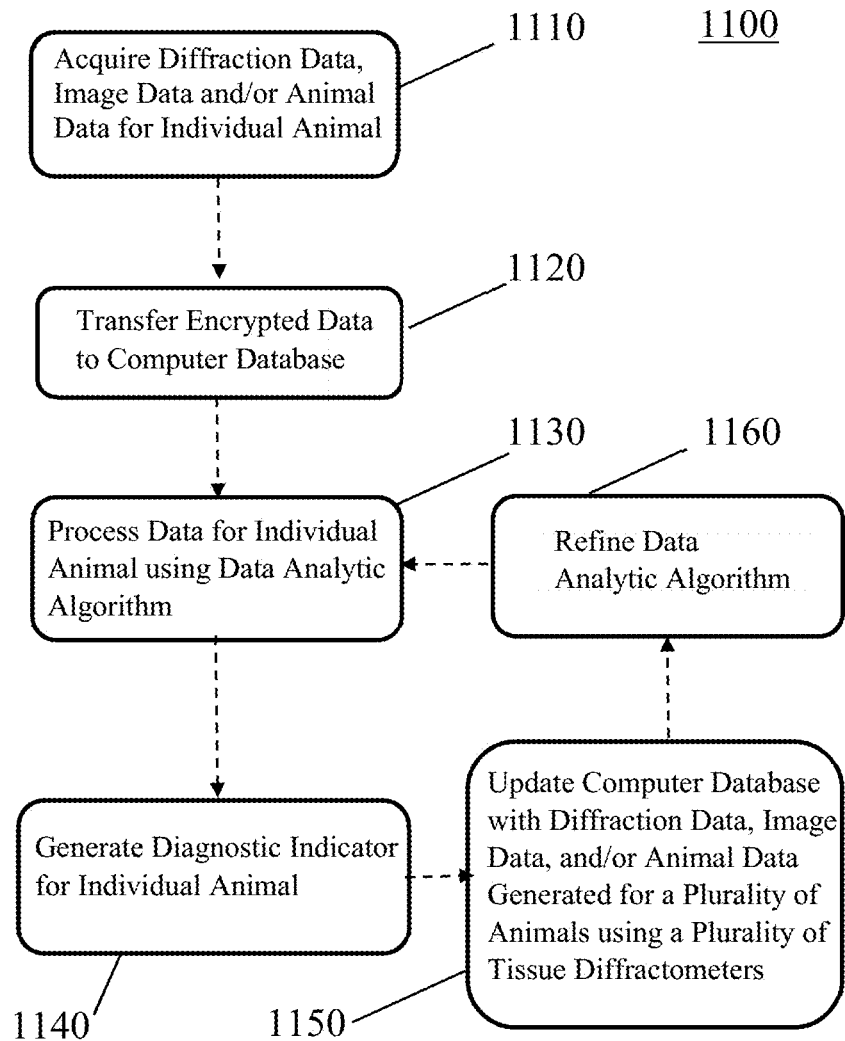
FIG. 8 shows an example schematic for a data collection and processing workflow.

FIG. 8 shows an example schematic for a data collection and processing workflow 1100. In an operation 1110, the process 1100 may comprise acquiring diffraction data, image data, animal data, or any combination thereof for an individual animal. The acquiring may be acquiring using an x-ray absorptive instrument, a diffraction-based instrument, or a combination thereof. For example, a combined absorptive instrument and diffraction instrument can acquire both absorptive images and tissue diffraction patterns. The acquiring may be in a single session. For example, animal data comprising medical history and ancestral medical information can be acquired through an interview with the animal owner before a x-ray analysis is taken. The acquiring may be over a plurality of sessions. For example, a time series of x-ray images and diffraction patterns can be taken over a period of time to track a change in a cancer state of a animal. The image data, diffraction data, animal data, or any combination thereof may be data as described elsewhere herein. The acquiring may be performed by one or more tissue diffractometers as described elsewhere herein.

In another operation 1120, the process 1100 may comprise transferring encrypted data to a computer database. The encrypted data may comprise image data, diffraction pattern data, animal data, or any combination thereof for one or more individual animal s. For example, the encrypted data can comprise all of the data taken from a radiology clinic in a day. In another example, the encrypted data may be data from the owner of an animal whose animal is served by a radiological veterinary clinic. The encrypted data may be encrypted using an asymmetric key encryption, a symmetric key encryption, or the like. The encrypted data may be encrypted by a computing device local to where the data was generated (e.g., a computer operatively coupled to a tissue diffractometer). The encrypted data may be stored locally before being transferred to the computer database. The encrypted data may be streamed (e.g., transferred in real-time or substantially real-time) to the computer database. The computer database may be a local computer database (e.g., a local computing cluster housed in the same facility as where the data was acquired) or a remote computer database (e.g., a cloud computing database). The encrypted data may be uncompressed data or uncompressed data.

In another operation 1130, the process 1100 may comprise processing data for the individual animal using a data analytics algorithm. The processing may be performed on one or more computer processors as described elsewhere herein. The processing may be encoded on a non-transitory computer readable medium. The data analytics algorithm may be a statistical analysis algorithm and/or a machine learning algorithm. The data analytics algorithm may be a convolutional neural network as described elsewhere herein. The data analytics algorithm may perform pre-processing, processing, and/or post-processing of diffraction data, image data, animal data, or any combination thereof. The pre-processing may comprise denoising (e.g., removing nose from the data), normalizing (e.g., standardizing data properties such as size, black level, maximum intensity, etc.), segmentation (e.g., dividing the data into sections comprising different features), masking (e.g., applying one or more masks to the data), enhancing edges and/or features, or the like, or any combination thereof. The processing may comprise determining a presence or absence of a feature in the data, clustering data (e.g., clustering images based on the presence or absence of a feature), predicting a presence or absence of a feature in new data (e.g., using previously acquired images to generate a prediction of a presence of a feature in a new set of data), or the like, or any combination thereof. The post-processing may comprise formatting denoising, normalizing, masking, enhancing properties (e.g., contrast, edges), or the like, or any combination thereof.

In another operation 1140, the process 1100 may comprise generating a diagnostic indicator for the individual animal. The diagnostic indicator may be a quantitative-diagnostic indicator. The computer aided diagnostic indicator may be a computer readable report, a human readable report, or both. For example, the computer aided diagnostic indicator can be a report displayed on a user interface of a device. The diagnostic indicator may comprise information about a likelihood of a presence of a feature in the data (e.g., a presence of breast cancer in x-ray absorptive data and diffraction data), a severity of a presence of a feature (e.g., a prognosis based on the severity of the feature), one or more suggested treatments (e.g., a suggestion of a mastectomy for a severe breast cancer), additional information (e.g., locations of resources to help the animal owner understand the diagnostic indicator), animal data (e.g., the name of the animal the indicator is for), or the like, or any combination thereof. The diagnostic indicator may be generated on a same computer system as the data analytics algorithm was run on. The diagnostic indicator may be held until the animal owner or their veterinary services provider provides an input. The input may be a payment (e.g., a payment from the animal, a payment from the animal's insurance), an agreement for the animal's data to be used for training and/or validating future data analytics algorithms, or the like, or any combination thereof. For example, the animal owner can be informed that the diagnostic indicator is ready, and that the animal owner can sign a waiver allowing use of the animal's data.

In another operation 1150, the process 1100 may comprise updating the computer database with the image data, diffraction data, animal data, or any combination thereof generated for a plurality of animal s using a plurality of tissue diffractometers. The updating may make additional data available to train a new data analytics algorithm or update an existing data analytics algorithm. The computer database may be updated with indicators of a confirmation of an indication made in a diagnostic indicator. For example, the database can be updated with information regarding the surgical confirmation of cancer in an animal for whom the diagnostic indicator indicated a likelihood of cancer. This updating may provide a confirmation of positive or negative results that can improve the accuracy of future diagnostic indicators. The data may be agglomerated for the plurality of animals to generate a general classifier. For example, a database of breast images and diffraction patterns can be used to generate a classifier for breast tissue. In another example, a database of brain images and diffraction patterns can be used to generate a classifier for brain tissues.

In another operation 1160, the process 1100 may comprise refining the data analytics algorithm. The refining may comprise generating a new data analytics algorithm. The refining may comprise an updating of weights or other components within the data analytics algorithm. For example, the neural weights of a neural network can be updated based on the additional data from the plurality of animals. The refining of the data analytics algorithm may improve the sensitivity, specificity, accuracy, or any combination thereof of the data analytics algorithm. The refined data analytics algorithm may be used to process the data for another animal (e.g., used as the data analytics algorithm of operation 1130).

The methods and systems of the present disclosure may be applied for diagnostic purposes. For example, the presence of a cancer in a breast of an animal can be diagnosed using a combination of x-ray absorptive and diffraction pattern data. The diagnostic purposes may include cancer diagnosis, muscular condition diagnoses (e.g., muscular degeneration), optometric diagnoses (e.g., corneal damage, other eye diseases), bone condition diagnoses (e.g., osteoporosis), other tissue diagnoses (e.g., brain degeneration), or the like, or any combination thereof. The generation of diffraction pattern data may be combined with x-ray absorptive instruments, chest x-ray instruments, skull x-ray instruments, limb x-ray instruments, C-arm xray instruments, or the like. For example, a C-arm x-ray instrument can comprise two optical paths, one for absorptive imaging and another for diffraction pattern data generation.

Figure 9:
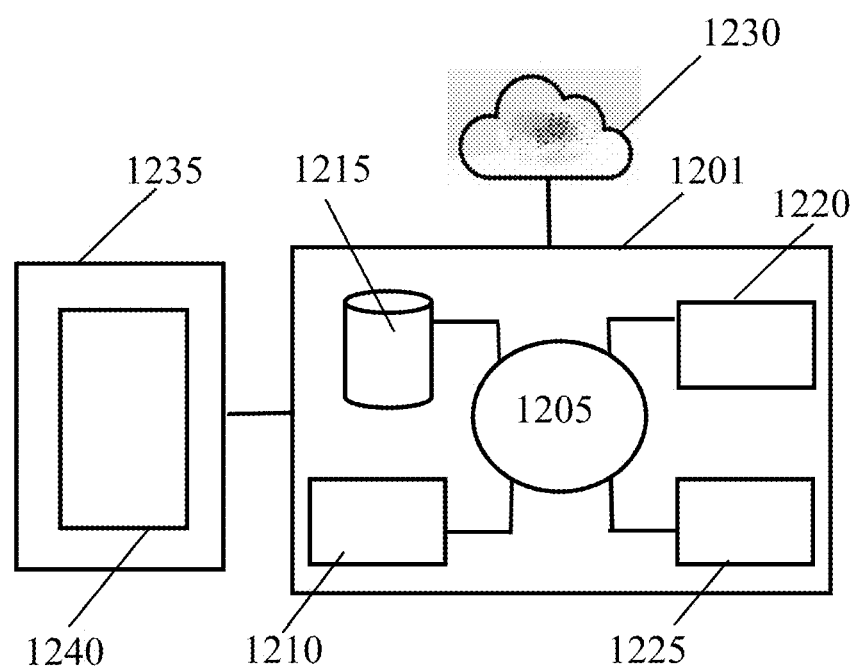
FIG. 9 shows a computer system that is programmed or otherwise configured to implement methods provided herein.

The present disclosure also provides computer systems that are programmed to implement methods of the disclosure. FIG. 9 shows a computer system 1201 that is programmed or otherwise configured to implement methods described elsewhere herein (e.g., obtaining data from one or more tissue diffractometers, processing the data, etc.). The computer system 1201 can regulate various aspects of the present disclosure, such as, for example, the processing of image data, diffraction pattern data, animal data, or any combination thereof. The computer system 1201 can be an electronic device of a user or a computer system that is remotely located with respect to the electronic device. The electronic device can be a mobile electronic device. The computer system 1201 may be a post-classical computer system (e.g., a quantum computing system).

The computer system 1201 includes a central processing unit (CPU, also "processor" and "computer processor" herein) 1205, which can be a single core or multi core processor, or a plurality of processors for parallel processing. The computer system 1201 also includes memory or memory location 1210 (e.g., random-access memory, read-only memory, flash memory), electronic storage unit 1215 (e.g., hard disk), communication interface 1220 (e.g., network adapter) for communicating with one or more other systems, and peripheral devices 1225, such as cache, other memory, data storage and/or electronic display adapters. The memory 1210, storage unit 1215, interface 1220 and peripheral devices 1225 are in communication with the CPU 1205 through a communication bus (solid lines), such as a motherboard. The storage unit 1215 can be a data storage unit (or data repository) for storing data. The computer system 1201 can be operatively coupled to a computer network ("network") 1230 with the aid of the communication interface 1220. The network 1230 can be the Internet, an internet and/or extranet, or an intranet and/or extranet that is in communication with the Internet. The network 1230 in some cases is a telecommunication and/or data network. The network 1230 can include one or more computer servers, which can enable distributed computing, such as cloud computing. The network 1230, in some cases with the aid of the computer system 1201, can implement a peer-to-peer network, which may enable devices coupled to the computer system 1201 to behave as a client or a server.

The CPU 1205 can execute a sequence of machine-readable instructions, which can be embodied in a program or software. The instructions may be stored in a memory location, such as the memory 1210. The instructions can be directed to the CPU 1205, which can subsequently program or otherwise configure the CPU 1205 to implement methods of the present disclosure. Examples of operations performed by the CPU 1205 can include fetch, decode, execute, and writeback.

The CPU 1205 can be part of a circuit, such as an integrated circuit. One or more other components of the system 1201 can be included in the circuit. In some cases, the circuit is an application specific integrated circuit (ASIC).

The storage unit 1215 can store files, such as drivers, libraries and saved programs. The storage unit 1215 can store user data, e.g., user preferences and user programs. The computer system 1201 in some cases can include one or more additional data storage units that are external to the computer system 1201, such as located on a remote server that is in communication with the computer system 1201 through an intranet or the Internet.

The computer system 1201 can communicate with one or more remote computer systems through the network 1230. For instance, the computer system 1201 can communicate with a remote computer system of a user (e.g., a cloud server). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1201 via the network 1230.

Methods as described herein can be implemented by way of machine (e.g., computer processor) executable code stored on an electronic storage location of the computer system 1201, such as, for example, on the memory 1210 or electronic storage unit 1215. The machine executable or machine-readable code can be provided in the form of software. During use, the code can be executed by the processor 1205. In some cases, the code can be retrieved from the storage unit 1215 and stored on the memory 1210 for ready access by the processor 1205. In some situations, the electronic storage unit 1215 can be precluded, and machine-executable instructions are stored on memory 1210.

The code can be pre-compiled and configured for use with a machine having a processer adapted to execute the code, or can be compiled during runtime. The code can be supplied in a programming language that can be selected to enable the code to execute in a precompiled or as-compiled fashion.

Aspects of the systems and methods provided herein, such as the computer system 1201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1201 can include or be in communication with an electronic display 1235 that comprises a user interface (UI) 1240 for providing, for example, an interface for a healthcare or an individual animal to upload image data, diffraction pattern data, animal data, or any combination thereof to a computer database. Examples of UI's include, without limitation, a graphical user interface (GUI) and web-based user interface. [00106] Methods and systems of the present disclosure can be implemented by way of one or more algorithms. An algorithm can be implemented by way of software upon execution by the central processing unit 1205. The algorithm can, for example, be a machine learning algorithm as described elsewhere.

Although aspects of the present disclosure have been described in detail with reference to certain implementations, persons possessing ordinary skill in the art to which this disclosure pertains will appreciate that various modifications and enhancements may be made without departing from the spirit and scope of the claims that follow. Any feature, whether preferred or not may be combined with any other feature whether preferred or not. It should be understood that various alternatives to the embodiments of the invention described herein can be employed in practicing the invention. It is intended that the following claims define the scope of the invention and that methods and structures within the scope of these claims and their equivalents be covered thereby. The appended claims are not to be interpreted as including means-plus-function limitations, unless such a limitation is explicitly recited in a given claim using the phrase "means for."

What is claimed is:

1. An animal-tissue analysis and communication system that produces a quantitative diagnostic indicator for animal-tissue analyzed by the system, comprising:
   an animal-tissue-analyzer subsystem that includes at least two diffractometers, each being located in different geographic locations, wherein one of the diffractometers is configured to analyze animal tissue and to produce a quantitative-diagnostic indicator; and
   a two-way communication subsystem constructed to allow the animal-tissue-analyzer subsystem to send and receive information relevant to the quantitative-diagnostic indicator.

2. The system of claim 1, wherein at least one of the diffractometers is operatively coupled to a computer database over a network, and is configured for acquisition of animal-tissue data chosen from the group consisting of in situ image data, in situ diffraction pattern data, and subject data, and transfer of the animal-tissue data to the computer database over the network.

3. The system of claim 2, wherein at least one computer processor is operatively coupled to the at least one diffractometer operatively coupled to the computer database, and wherein the at least one computer processor is configured to receive the animal-tissue data from the at least one diffractometer, transmit the animal-tissue data to the computer database; and process the animal-tissue data using a data analytics algorithm that provides a computer-aided quantitative-diagnostic indicator for a given animal-tissue sample.

4. The system of claim 3, further comprising a user interface that allows an individual animal owner or a veterinary-services provider to upload the animal-tissue data.

5. The system of claim 4, wherein the user interface is further configured to allow an individual animal owner or a veterinary services provider to make payments or upload a consent form signed by individual animal owner.

6. The system of claim 3, wherein the data analytics algorithm comprises a statistical analysis of diffraction pattern data or a function thereof.

7. The system of claim 6, wherein the statistical analysis comprises determination of a pairwise distance distribution function, determination of a Patterson function, a calculation of a Porod invariant, a cluster analysis, a dispersion analysis, determination of one or more molecular structural periodicities, or any combination thereof.

8. The system of claim 6, wherein the statistical analysis comprises a determination of a structural periodicity of collagen, at least one lipid sample, and a tissue sample.

9. The system of claim 6, wherein the data analytics algorithm comprises a machine learning algorithm.

10. The system of claim 9, wherein the machine learning algorithm comprises a supervised learning algorithm, an unsupervised learning algorithm, a semi-supervised learning algorithm, a reinforcement learning algorithm, a deep learning algorithm, or any combination thereof.

11. The system of claim 9, wherein the machine learning algorithm is a deep learning algorithm.

12. The system of claim 11, wherein the deep learning algorithm is a convolutional neural network, a recurrent neural network, or a recurrent convolutional neural network.

13. The system of claim 9, wherein the machine learning algorithm is trained using a training dataset comprising image data, diffraction pattern data, subject data, or any combination thereof stored in the computer database for a specific pathology or physiological norm group.

14. The system of claim 13, wherein the training dataset is updated as new in situ image data, in situ diffraction pattern data, animal data, or any combination thereof, and uploaded to the computer database.

15. The system of claim 2, wherein a diffractometer of the at least one diffractometer operatively coupled to the computer database comprises a data encryption device that includes a global positioning system (GPS) positioning sensor and generates encrypted in situ image data, in situ diffraction pattern data, animal data, or any combination thereof, which encrypted in situ image data, in situ diffraction pattern data, animal data, or any combination thereof that is transferred to the computer database tracks changes in the geographic location of the diffractometer comprising the data encryption device.

16. The system of claim 2, wherein the at least one diffractometer operatively coupled to the computer database is configured to perform small angle x-ray scattering (SAXS) measurements.

17. The system of claim 16, wherein the at least one diffractometer operatively coupled to the computer database is configured to perform wide angle x-ray scattering (WAXS) measurements.

18. The system of claim 2, wherein the computer database resides on a central server.

19. The system of claim 2, wherein the computer database resides in the cloud.

20. The system of claim 2, wherein the animal-tissue data is depersonalized prior to transfer.

21. The system of claim 20, wherein a key for mapping depersonalized animal-tissue data is stored in a local institutional database or in individual personal files of an animal owner.

22. The system of claim 1, the animal-tissue-analyzer subsystem is further configured to produce the quantitative-diagnostic indicator using animal data that relates to an animal tissue sample, and comprises an animal's age, sex, weight, body condition score (BCS), ancestry data, genetic data, behavioral data, or any combination thereof.

23. The system of claim 1, wherein the quantitative-diagnostic indicator includes an indication of a likelihood that a corresponding animal has cancer.

24. The system of claim 23, wherein the indication is for the likelihood that the corresponding animal has breast cancer.

25. The system of claim 24, wherein the quantitative-diagnostic indicator includes a diagnosis that the corresponding animal has a cancer.

26. The system of claim 25, wherein the diagnosis is of breast cancer.

\* \* \* \* \*